United States Patent [19]

Suzuki et al.

[11] Patent Number: 4,977,811
[45] Date of Patent: Dec. 18, 1990

[54] ANGLE SENSOR FOR MUSICAL TONE CONTROL

[75] Inventors: Hideo Suzuki; Shunichi Matsushima; Masahiko Obata; Takamichi Masubuchi; Masao Sakama, all of Hamamatsu, Japan

[73] Assignee: Yamaha Corporation, Hamamatsu, Japan

[21] Appl. No.: 352,410

[22] Filed: May 16, 1989

[30] Foreign Application Priority Data

May 18, 1988 [JP] Japan ................... 63-65706

[51] Int. Cl.⁵ .............. G10H 1/32; G01B 7/30; A61B 5/103; H01C 10/32
[52] U.S. Cl. ................ 84/600; 84/DIG. 24; 33/1 PT; 310/338; 338/13; 338/162
[58] Field of Search ........ 84/600, 723, 730, DIG. 24; 128/782; 33/1 N, 1 PT; 310/338, 355; 338/13, 49, 162; 73/DIG. 4

[56] References Cited

U.S. PATENT DOCUMENTS 4,667,685 5/1987 Fine ..................... 128/782
4,905,560 3/1990 Suzuki et al. ............ 84/600

OTHER PUBLICATIONS

Published European Application No. 264,782 to Hiyoshi, 4/1988.

Primary Examiner—W. B. Perkey
Attorney, Agent, or Firm—Spensley Horn Jubas & Lubitz

[57] ABSTRACT

The present invention relates to an angle sensor for musical tone control which controls a musical tone in response to changing angles at an articulation of the human body. Both ends of a pair of plate members are coupled pivotally and movably around an axis parallel to both faces of plate members. This pair of plate members are attached on the interior side of articulation of the human body by attaching means to generate a signal in response to the bending motion of the articulation. Thus, a musical tone control signal in response to the bending angles is outputted from detecting means which is placed on the plate members to control musical tone.

4 Claims, 3 Drawing Sheets

ANGLE SENSOR FOR MUSICAL TONE CONTROL

BACKGROUND OF THE INVENTION

1. Field of the Invention

The present invention relates to an angle sensor for musical tone control which can control a musical tone in response to changing angles at an articulation of the human body.

2. Prior Art

A musical tone is usually generated by playing piano, violin, or the like, or by the vocal cords of a singer. Such a musical tone can also be produced by a musical control apparatus which converts the movement of the human body into a musical tone in response to a performed motion of such as in aerobic dancing.

However, when a performer moves vigorously, the musical control apparatus can not produce a desirable musical tone because of interference by vigorous movement.

SUMMARY OF THE INVENTION

It is accordingly an object of the present invention to provide an angle sensor for musical tone control which can control musical tone in response to the bending of articulations of a performer without interfering with the motion of the performer during vigorous movement.

In an aspect of the present invention, there is provided an angle detector for musical tone control comprising: a pair of plate members coupled pivotally and movably around an axis which is parallel to both faces of said plate members; detecting means for detecting a signal in response to an angle when said pair of plate members pivot in relation to each other around said axis, said detecting means generating a musical tone control signal in response to said signal to control a musical tone; attaching member for arranging said pair of plate members on the interior side of the bending articulation so that said pair of plate members pivot in relation to each other around said axis in response to the bending motion of articulation.

DESCRIPTION OF THE PREFERRED EMBODIMENT

Hereinafter, an embodiment of the present invention is described by reference to the drawings.

Figure 1:
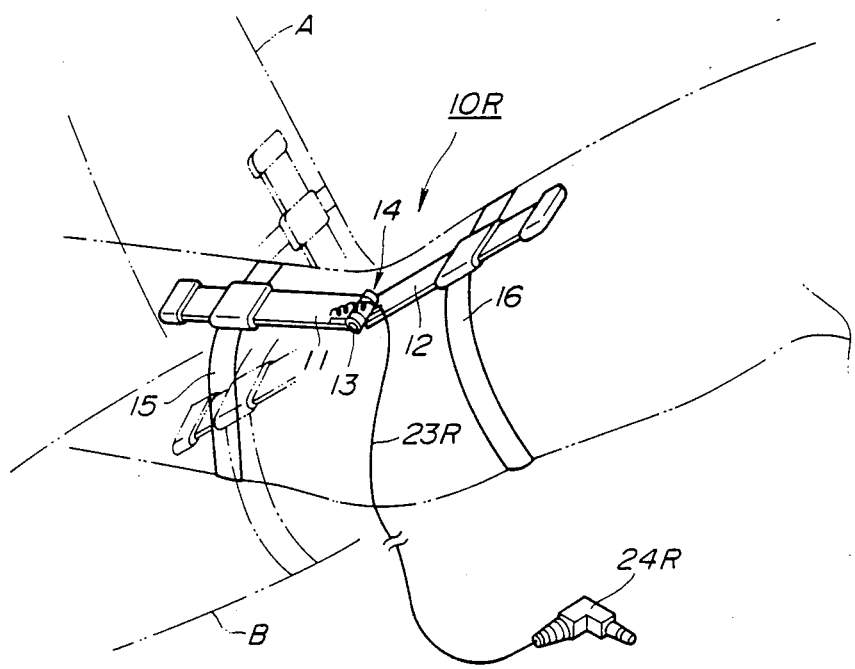
FIG. 1 is a perspective view showing a construction of the angle sensor for musical tone control in an embodiment.
Figure 2:
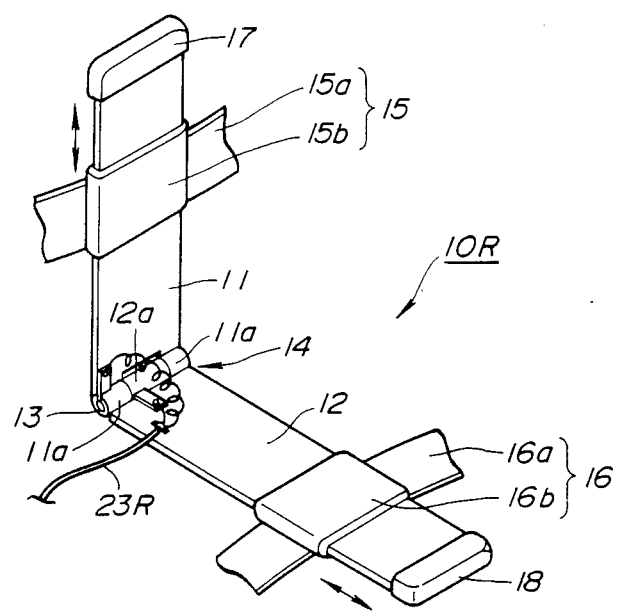
FIG. 2 is an enlarged perspective view showing the angle detector.
Figure 3:
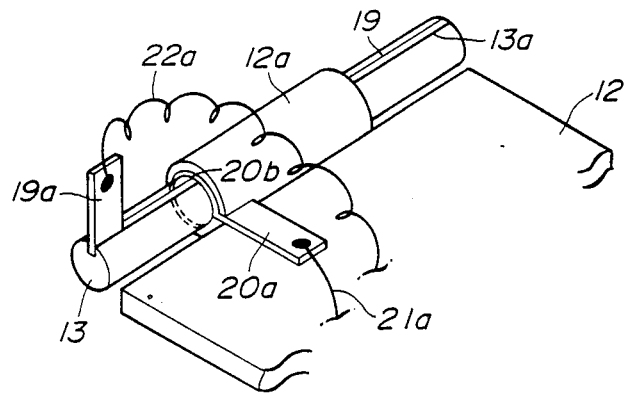
FIG. 3 is a perspective view, partially cut away, showing a construction of the main portion of the angle detector.

FIGS. 1 to 3 show a construction of right elbow angle detector 10R for musical tone control in an embodiment.

This angle detector 10R comprises a pair of plate members 11 and 12 coupled pivotally and movably around an pivot 13 which is parallel to both faces of a pair of plate members 11 and 12; a detecting portion 14 for detecting a signal in response to an angle when a pair of plate members 11 and 12 pivot in relation to each other around pivot 13, and generate a musical tone control signal in response to said signal to control a musical tone; attaching bands 15 and 16 for arranging a pair of plate members 11 and 12 on the interior side of the right elbow so that a pair of plate members 11 and 12 pivot in relation to each other around pivot 13 in response to the bending motion of right elbow.

The attaching band 15 comprises a band 15a attached to the wrist side, or lower arm of the performer, and a retainer 15b attached to band 15a to retain plate member 11 movable along arrows shown in FIG. 2. Similarly, the attaching band 16 comprises a band 16a attached to the shoulder side, or upper arm of the performer, and a retainer 16b attached to band 16a to retain plate member 12 movable along arrows. The band 15a and 16a are made of an elastic material, and stoppers 17 and 18 are fixed to each end portion of plate members 11 and 12 to prevent plate members 11 and 12 from coming off.

The detecting portion 14 is described hereinafter. The plate members 11 and 12, and pivot 13 are made of plastic, or the like, which is an electrical insulator. In FIG. 3, a groove 13a is formed on the surface of pivot 13 in the longitudinal direction, and a slide contact 19 is affixed in groove 13a. Both end portions of pivot 13 are fixed in tubular portions 11a and 11a as shown in FIG. 2, in which both tubular portions 11a and 11a are rigidly or integrally formed at the edge portion of plate member 11; while a tubular portion 12a is rigidly or integrally formed at the edge portion of plate member 12 and a tubular resistance element 20b is immovably inserted into tubular portion 12a as shown in FIG. 3. In addition, the pivot 13 is slidably inserted into tubular resistance element 20b so as to contact the inner surface thereof. A terminal 20a is extended from an outer surface of tubular resistance element 20b through a cutting portion of tubular portion 12a and lead 21a is bonded thereto; while a terminal 19a is rigidly affixed in the end portion of slide contact 19 and groove 13a, and lead 22a is bonded thereto. These leads 21a and 22a are connected to connector 24R through cable 23R as shown in FIG. 1.

The above-described right elbow angle detector 10R is attached to the right arm as shown in FIG. 1. Accordingly, when the right arm is bent to the position shown by the double dotted line A shown in the drawing, or when the right arm is straightened to the position shown by the double dotted line B, plate members 11 and 12 are pivoted around pivot 13 in response to the bending of the arm. By pivoting plate members 11 and 12, the slide contact 19 moves along the inner surface of tubular resistance element 20b. Thus, the resistance between terminal 20a of tubular resistance element 20b and terminal 19a of slide contact 19 is changed in response to the position of slide contact 19, or the bending angle of the right arm.

According to the above-described embodiment, in FIG. 2, the ends of plate members 1 1 and 12 are pivotally and movably coupled by pivot 13 parallel to both faces of plate members 11 and 12, and in addition, detecting portion 14 placed in the pivot portion of plate members 11 and 12, is attached on the interior side of arm near the axis of bending, and in addition, plate members 11 and 12 slide through retainers 15b and 16b in response to the bending and straightening of arm, so that the angle detector 10R does not interfere with the arm motion of the performer and does not move out of position when the performer moves vigorously.

Heretofore, the angle detector 10R for the right arm has been described. Since the angle detector 10L is identical in construction, the description of the construction of angle detector 10L is omitted for the sake of simplicity.

Figure 4:
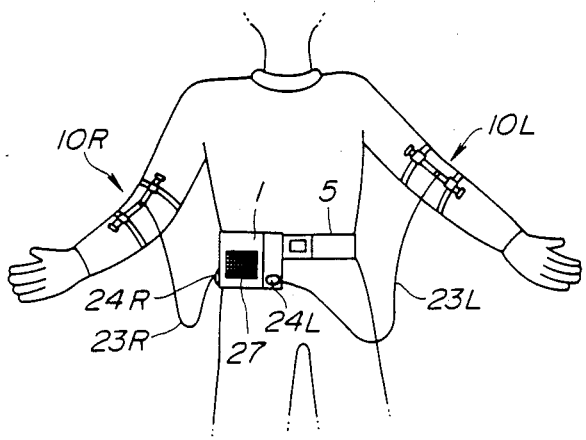
FIG. 4 is a front view showing the entire construction of the angle sensor.

FIG. 4 shows a musical tone control apparatus being worn by a performer, in which the apparatus comprises an angle detector 10R to be attached to the right arm, an angle detector 10L to be attached to the left arm, and a controller 1 to be attached to belt 5. The angle detector 10R is connected to controller 1 through cable 23R and connector 24R, while the angle detector 10L is connected to controller 1 through cable 23L and connector 24L. Accordingly, the apparatus can control musical tone so as to output a tone pitch of musical tone from speaker 27 incorporated in controller 1 in response to the combination of the bending angles of the right and left elbows. Controller 1 is described later.

Figure 5:
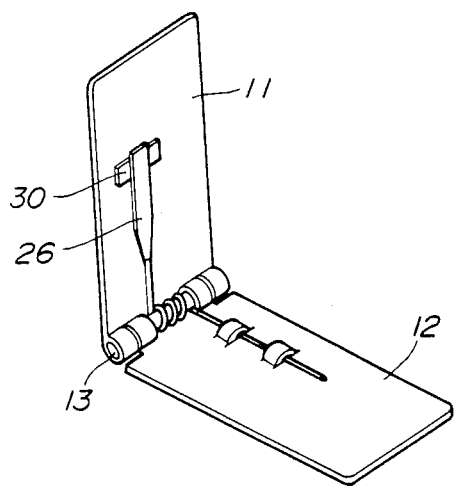
FIG. 5 is a perspective view showing a construction of the angle detector in another embodiment.

FIG. 5 shows another embodiment of the present invention. In this embodiment, both tubular portions of plate members 11 and 12 are engaged by a hinge, and pivot an pivot 13 passes through from one end of the tubular portion to the other. A spring 26 is around pivot 13, a middle portion of which is exposed between tubular portions formed with plate member 12. One end of spring 26 is fixed at plate member 12, while the other end makes contact to a piezoelectric element 27 by urging of spring 26. This arrangement changes signal level from piezoelectric element 27 in response to the bending angle of plate members 11 and 12 when plate members 11 and 12 pivot around axis 13.

Figure 6:
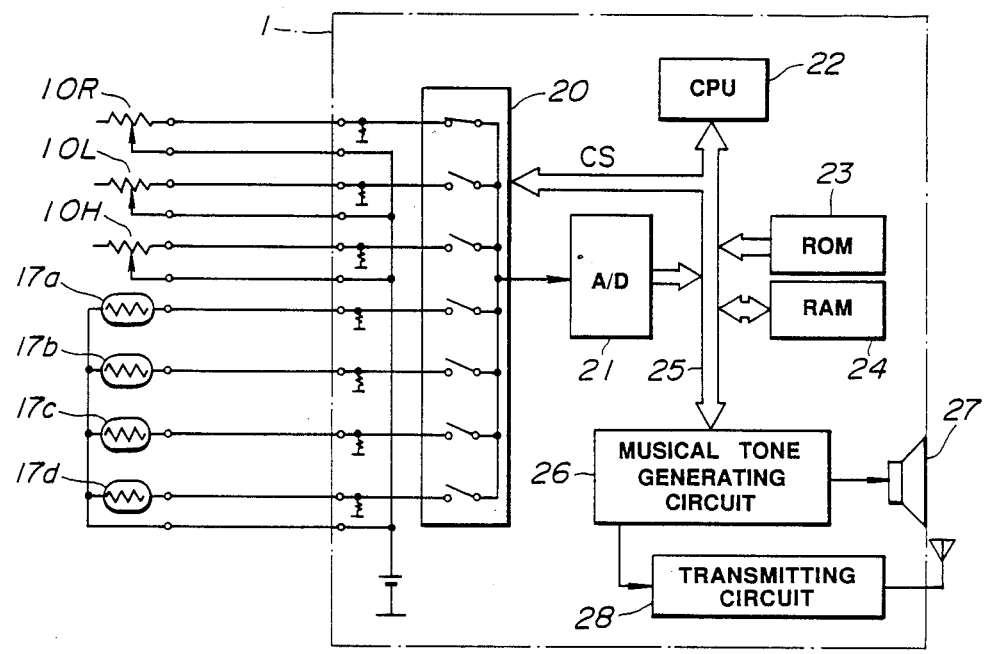
FIG. 6 is a block diagram showing an electrical control construction of the musical tone control apparatus.

Next, controller 1 is described by reference to FIG. 6. In FIG. 6, the above-described angle detectors 10R and 10L are connected to controller 1. Another angle detector 10H is also connected to controller 1. This angle detector 10H is not shown in FIG. 4, but attaching to the wrist, for example. Another detectors, so-called finger pressure sensing elements 17a, 17b, 17c, and 17d are connected to controller 1 which are not shown in FIG. 4. These finger pressure sensing elements 17a, 17b, 17c, and 17d are used for detecting finger pressure to transmit a corresponding signal to controller 1.

The description of controller 1 therefore includes angle detector 10H and finger pressure sensing elements 17a, 17b, 17c, and 17d. In FIG. 6, numeral 20 designates an analog multiplexer for seven channels, selected terminals of which receive channel-select signal CS. The analog multiplexer 20 selects one of angle detectors 10R and 10L, and 10H, and from finger pressure sensing elements 17a to 17d, based on channel-select signal CS, and then the selected signal is outputted therefrom. Numeral 21 designates an A-D converter which converts the detecting signal supplied from analog multiplexer 20 into digital detecting data, including predetermined bits. Numeral 22 designates a CPU (central processing unit). Numeral 23 designates a ROM (read only memory), which stores programs used by CPU 22. Numeral 24 designates a RAM (random access memory) used for a work area. CPU 22 supplies channel-select signal CS to analog multiplexer 20, and this analog multiplexer 20, in turn, scans the output signals from angle detectors 10R and 10L, and 10H, and from finger pressure sensing elements 17a to 17d at high speed. Furthermore, the CPU 22 classifies the bending angles of right and left elbows into four groups based on the detecting data supplied from angle detectors 10R and 10L, and which is converted by A-D converter 21. Based on the result of the classification, CPU 22 generates keycode data KC which indicates a predetermined tone pitch in response to the combination of the bending angles of right and left elbows. The CPU 22 also classifies the bending angles of the right wrist into three groups based on detecting data supplied from angle detector 10H and converted by A-D converter 21. Based on the result of the classification, the CPU 22 generates tone volume data VOL indicative of the tone volume (high, medium, or low) in response to the bending angle of the right wrist. The CPU 22 also decides which finger or fingers are bent among the index finger, middle finger, ring finger, or little finger. Based on the result of this decision, the CPU 22 generates tone color-indicating data TD indicative of a predetermined tone color (piano, organ, flute, sax, clarinet or the like) in response to the combination of the bent finger or fingers. These key-code data KC, tone volume data VOL, and tone color-indicating data TD which are generated by CPU 22 ar supplied to a musical tone signal generating circuit 26 through a bus line 25. The musical tone signal generating circuit 26 generates a musical tone signal indicative of tone pitch in response to a supplied key-code data KC, tone volume in response to tone volume data VOL, and tone color indicated by tone color-indicating data TD. The musical tone signal generated from musical tone signal generating circuit 26 is supplied to speaker 27, from which the corresponding musical tone is generated. Numeral 28 designates a transmitting circuit which transmits musical tone signal outputted from musical tone signal generating circuit 26 by a wireless means.

According to the above described construction, the musical tone control apparatus can change the tone pitch of a musical tone outputted from speaker 27 which is incorporated in controller 1, in response to the detecting combination of bending angles of the right and left elbows of the performer; set the tone volume of musical tone into one of three groups in response to the bending angle of the right wrist of the performer; and furthermore, change the tone color of musical tone in response to the combination of bending finger or fingers. In other words, this apparatus can control the musical tone in response to the motion of the performer.

The preferred embodiment described herein is illustrative and not restrictive; the scope of the invention is indicated by the appended claims and all variations which fall within the claims are intended to be embraced therein.

What is claimed is:

1. An angle sensor for musical tone control comprising:
   a pair of plate members coupled pivotally and movably around an axis which is parallel to both faces of said plate members;
   detecting means for detecting a signal in response to an angle when said pair of plate members pivot in relation to each other around said axis, said detecting means generating a musical tone control signal in response to said signal to control a musical tone;
   attaching member for arranging said pair of plate members on the interior side of the bending articulation so that said pair of plate members pivot in relation to each other around said axis in response to the bending motion of articulation.

2. An angle sensor for musical tone control according to claim 1 wherein said detecting means comprises a tubular resistance portion integrally or rigidly formed at one end of said plate members, and a slide contact formed with said axis which is slidably inserted into said tubular resistance portion to change resistance in response to the bending angle of said plate members.

3. An angle sensor for musical tone control according to claim 1 wherein said detecting means comprises a spring and a pressure sensing element urged by said spring, in which one end of said spring is fixed at one plate member and the other end is urged to said pressure sensing element placed on the other plate member to output signals in response to the bending angle of said plate members.

4. An angle sensor for musical tone control according to claim 1 wherein said attaching member comprises a band having a retainer, in which said retainer slidably holds said plate member in the longitudinal direction of said plate members in response to the movement of articulation.

* * * * *